United States Patent [19]

Resnick

[11] 4,251,544
[45] Feb. 17, 1981

[54] FUNGICIDAL PROCESS USING 1-(ALKYLACYL) GUANIDINES

[75] Inventor: Bruce M. Resnick, West Paterson, N.J.

[73] Assignee: GAF Corporation, New York, N.Y.

[21] Appl. No.: 76,682

[22] Filed: Sep. 19, 1979

[51] Int. Cl.³ .......................................... A01N 37/18
[52] U.S. Cl. ................................................... 424/320
[58] Field of Search ........................................ 424/320

[56] References Cited

U.S. PATENT DOCUMENTS

| | | | |
|---|---|---|---|
| 2,378,724 | 6/1945 | Oldham | 260/29 |
| 2,408,694 | 10/1946 | Simons et al. | 260/564 |
| 2,545,423 | 3/1951 | Duerr | 95/8 |
| 2,734,904 | 2/1956 | Burtner | 260/295 |
| 2,867,562 | 1/1959 | Lamb | 424/316 |
| 3,142,615 | 7/1964 | Wehner | 424/326 |
| 3,222,398 | 12/1965 | Brown et al. | 260/565 |
| 3,564,607 | 2/1971 | Breuer | 260/429.9 |
| 3,564,608 | 2/1971 | Breuer | 260/559 |
| 3,632,333 | 1/1972 | Breuer | 71/118 |
| 3,759,991 | 9/1973 | Manhs | 424/322 |
| 3,794,685 | 2/1974 | Diamond et al. | 260/565 |
| 3,821,406 | 6/1974 | Diamond et al. | 424/326 |
| 3,996,232 | 12/1976 | Diamond et al. | 424/267 |
| 4,099,956 | 7/1978 | Pilgram | 71/120 |

*Primary Examiner*—Allen J. Robinson
*Attorney, Agent, or Firm*—James Magee, Jr.; Marilyn J. Maue

[57] ABSTRACT

This invention relates to a method of protecting plants, plant parts or soil from fungus attack by utilization of an effective amount of a 1-(alkylacyl) guanidine having the formula:

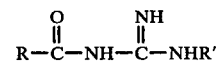

wherein R is alkyl of from 4 to 22 carbon atoms and R' is hydrogen or alkyl of 1 to 4 carbon atoms.

16 Claims, No Drawings

FUNGICIDAL PROCESS USING 1-(ALKYLACYL) GUANIDINES

BACKGROUND OF THE INVENTION

It has been generally accepted that the fungicidal activity of alkyl guanidines and their salts depends on the chain length of the N-alkyl group, i.e. 10 to 20 carbon atoms (Kirk-Othmer, Encyclopedia of Chemical Technology, 2nd Ed., Volume 10, page 225). However, these higher molecular weight amino groups cause the compounds to be highly insoluble in water and thereby complicate their use as aqueous sprays and treating solutions. The long carbon chain on the nitrogen also prevents penetration of the amino or guanidinyl moiety into plant tissue and thus hinders systemic activity. Accordingly, the activity of these compounds is of short duration and protection over an extended period requires a high replacement ratio.

The salts of alkylguanidines for the control of certain fungi are disclosed in U.S. Pat. Nos. 3,142,615 and 2,867,562. These compounds are highly selective to non-mutated forms of tree fungi; however, against the certain mutated and more resistant forms which are currently most troublesome, the alkyl guanidines and their salts show little or no fungicidal efficacy. Also, because of their moderately phytotoxic affect, the dosage levels of these compounds in the fungicidal composition cannot be appreciably increased. Accordingly, use of there fungicides has been restricted to the hardier woody plants.

The alkoxyphenylaceto guanidines of U.S. Pat. No. 2,734,904 and the phenylamino guanidines of U.S. Pat. Nos. 3,794,685; 3,821,406 and 3,996,232 are purported to have certain pharmaceutical uses; however, these disclosures fail to suggest any fungicidal use or properties for the compounds set forth therein.

The formation of thermosetting resins by conversion of aliphatic acyl guanidines to guanamines is the subject of U.S. Pat. No. 2,408,694. Also, U.S. Pat. No. 2,378,724 relates to the types of coating and textile finishing composition containing aliphatic acylguanidines which provide water proofing to the treated fabric. Certain other guanidines of U.S. Pat. No. 2,545,423 are used as barrier coatings to prevent dye diffusion. However, these patents also fail to suggest any mycological inhibition.

According to U.S. Pat. No. 3,759,991, carbamylated guanidines are found to be moderately effective fungicides; however, unusually high concentration of these compounds is required to bring about results. Unfortunately, these compounds also inhibit plant growth and cause stunting and abscission of new growth, which characteristics have prevented wide acceptance as fungicidal agricultural aids. The cyano-, aminol-, and carbazone- guanidines of U.S. Pat. Nos. 3,564,607; 3,564,608; 3,632,333 and 4,099,956 function only as herbicides and display no fungicidal properties whatever. Certain biguanides of the type disclosed in U.S. Pat. No. 3,222,398 possess limited fungicidal properties with selectivity to a specific fungus infection; but these moderately toxic compounds have only a narrow spectrum of efficacy. Finally the aliphatic guanidine xanthates of U.S. Pat. No. 2,198,774, while active fungicides, are highly toxic and therefore not suitable for use on crops.

Accordingly, it is an object of the present invention to overcome the above deficiencies and to provide fungicides which are innocuous to plant, animal or human contact.

Another object is to provide a fungicide of the guanidine type having better penetration of plant tissue;

Still another object is to provide a fungicide effective on a variety of fungi at low dosage levels;

Another object is to provide a guanidine which possess fungicidal activity for an extended duration;

Yet another object is to provide an economical and efficient process for the reduction, elimination or prevention of fungus infection in a plant, plant part or soil.

SUMMARY OF THE INVENTION

In accordance with this invention, there is provided a process for controlling infection or protecting from attack by fungus, plants, plant parts or soil by contacting the same with a fungicidally effective amount of a 1-(alkylacyl)guanidine. More particularly, the process of this invention concerns the fungicidal use of a 1-(alkylacyl)guanidine having the formula:

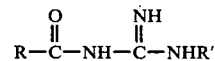

wherein R is alkyl having from 4 to 22 carbon atoms, preferably from 6 to 16 carbon atoms; and R' is hydrogen or alkyl of from 1 to 4 carbon atoms. More desirably, for better penetration of plant tissue, R' is hydrogen.

Suitably, the plant, plant part or soil is treated by spraying, immersing, dipping, dusting or otherwise contacting with a composition containing an effective amount of the fungicide of Formula I and an inert carrier therefor.

The process of the present invention is exemplified by protection of plants against attack by cucumber anthracnose, bean rust, pythium ultimum, erysiphe cichoracearum and rhizoctonia solani. However, it is to be understood that other fungi which infect crops are also arrested by treatment with the present fungicides.

DETAILED DESCRIPTION OF INVENTION

The fungicides of the present invention are known compounds and can be prepared by one of several conventional processes. For example, a guanidine can be refluxed for a period of from 10 minutes to 2 hours with a monobasic carboxylic acid ester containing the desired substitution according to the equation:

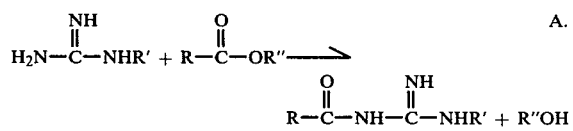

wherein R and R' have the meaning defined above and R" is alkyl of from 1 to 4 carbon atoms.

Exemplary of suitable monobasic aromatic acid esters which can be employed in this reaction are the methyl, ethyl, propyl or butyl butyrates, valerates, isovalerates, caproates, oenanthylates, pelargonates, caprates, undecylates, laurates, tridecylates, myristates, pentadecylates, oleates, palmitates, heptadecylates, stearates, nonadecylates, ecosanates, together with the branched chain isomers of the foregoing.

An alternative method for preparing the fungicidal agents of the present invention is illustrated by the reaction of a guanidine with an alkyl acyl halide having the desired substitution in the hydrocarbon moiety as is illustrated by the equation:

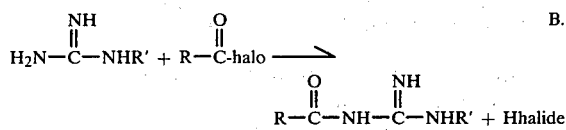
B.

wherein R and R' have the meaing recited above and halo is chloride, bromide or iodide. The reaction is effected at elevated temperature, preferably reflux, under atmospheric pressure or 10 to 50 psi for a period of time about 5 minutes to 5 hours or until the reaction is complete.

Still another method for the preparation of the fungicides used in the present process is illustrated by the equation:

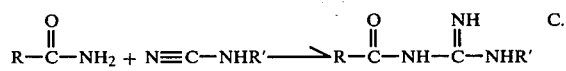
C.

wherein R and R' are as defined and designated above. The condensation reaction between the aromatic amide and the cyanamide is effected at a temperature between about 40° and about 200° C., preferably at reflux, under from about 10 to about 50 psi, more acceptably at atmospheric or autogenous pressure, for a period of from about 5 minutes to about 5 hours.

The mole ratio of guanidine reactant or cyanamide reactant to the ester, halide or amide coreactant in the above equations A. B. and C. can be varied in a range of between about 3:1 and about 1:5, depending upon the degree of conversion and the product desired.

The above reactions are effected under substantially anhydrous conditions by contacting the reactants, either in the presence or absence of an inert solvent. Suitable solvents include commercially available alcohols, ethers, ketones, alkanes including linear, branched or cyclic types of 5 or more carbon atoms, and aromatic solvents such as benzene, toluene and xylene. It is to be understood, however, that any of the other commercially available solvents which are inert to reactants in the selected reaction can be employed without departing from the scope of this invention. Also, any other convenient method for preparing the present fungicidal compounds is contemplated herein.

The fungicidal compositions of the invention are generally applied as a formulation containing a fungicidally effective amount of the active ingredient in an inert liquid or solid carrier. Accordingly, the formulation may take the form of a solution, a suspension, emulsion, wettable powder or dust for treating the foilage of the plants, or seeds, or the fruit thereof, prior to or after harvesting, or for addition to the soil, or treatment of plant roots, corms or rhisomes. When applied to a plant or plant part, the formulation can be employed before or after the onset of fungus infection; thus, the present fungicidal process can be employed as a preventative or a cure from fungus attack.

Although the present fungicidal agents can be applied as a dust in a particulate carrier such as talc, bentonite clay, kaolin, fullers earth, diatomaceous earth and other commercial dry carriers; the fungicides are preferably applied as a liquid spray when employed to treat plants or plant parts.

Suitable liquid carriers for use in the compositions of the invention include water, acetone, dimethylsulfoxide alcohols, such as methanol, propylene glycol, and diethylene glycol; N-methylpyrrolidone, mineral oil, vegetable oil, isoparaffinic hydrocarbons, such as naphtha or kerosene; ethyl ether, formamide, methylformamide, any of the solvents employed in the preparation of the fungicides and mixtures thereof, although many other available solvents may be used as well.

It is to be understood that the present mixture of fungicide and carrrier may include other active agricultural agents which do not diminish the affect of the present fungicides. These agents include other fungicides, herbicides, plant growth regulants, plant foods, nematocides, insecticides and the like, which can be incorporated into the present compositions at their recommended dosage levels. However, in the case of pesticide mixtures, somewhat less than the recommended dosage is often effective.

Examples of such mixtures of agriculturally active agents include the present fungicidal agents with not more than 60% by weight, preferably a minor amount of any auxiliary fungicide, of the commercial additive, e.g. Daconil, a fungicide of Diamond Shamrock Co. (tetrachloroisophthalonitrile as active ingredient); Vitavax, a soil fungicide of U.S. Rubber Co. (5,6-dihydro-2-methyl-1,4-oxanthiin-3-carboxanilide); Benomyl, i.e. methyl-1-(butycarbamoyl)-2-benzimidazole carbamate, a fungicide of E. I. Dupont; Sevin, i.e. 1-naphthyl-N-methyl-carbamate, an insecticide of Union Carbide Inc; Diuron, i.e. 3-(3,4-dichlorophenyl)-1,1-dimethylurea, a herbicide of E. I. Dupont; Dasanit, i.e. O-O-diethyl-O-(methylsufinyl) phosphorothioate, a nematocide of Chemgro Corp; Azodrin, i.e. O-O-dimethyl-O-(2-methylcarbamoyl-1-methylvinyl) phosphate, a pesticide of Shell development Corp; and the plant growth regulants ethephon, 3-(4-chlorophenyl)-1,1-dimethylurea; maleic hydrazide; cycloheximide; hydroxyethylhydrazine; tricontanol, abscisic acid; naphthoxy acetic acid; succinic acid-2,2-dimethyl hydrazine; gibberellic acid; N-methylpyrrolidone, and complexes of said cyclic amide or its polymer with ethephon and mixtures or intermixtures of the above and other known agricultural products.

It has been found that the present compounds are useful for the control of fungi which infect many living plants, particularly food crops. By way of example, they are demonstrated in processes for controlling or preventing attack by such fungi as bean rust, cucumber anthracnose and smut and soil fungi such as pythium ultium and rhizocotina solani; however, it is to be understood that the present fungicidal agents are also effective for protecting other plants or plant parts from attack by these and other destructive pathogenic fungi, particularly those of the Deuteromycetes, Basidiomycetes, and Pyrenomycetes types.

The compositions of the present invention, whether dusts or liquids, emulsions or suspensions, contain between about 5 and about 3,000 ppm, preferably between about 5 and about 800 ppm, of the present fungicidal agent. A convenient method of forming the liquid composition comprises first adding the present fungicide, alone or in admixture, to a blend containing a dispersant and a surfactant dissolved in a suitable solvent to form a liquid concentrate, and then diluting the concentrate with water to provide the desired concentration of the active fungicidal ingredient of the composition which can then be used for spraying a field of plant crops. In a typical preparation of such a spray formulation, the concentrate containing the active ingredient in an amount of about 10%, and the surfactant-dispersant of about 8%, by weight, in acetone as a solvent, is diluted with water to the aforementioned 5 to 3,000 ppm concentration range.

Alternatively, a wettable powder emulsion may be prepared for applying spray to the foliage or to the soil. The wettable power may be made by admixing the active ingredient with, e.g., bentonite, chalk, clay, diatomaceous earth, fuller's earth, mica, silica, talc, ground slate or any of the other usual particulate extenders for agricultural chemicals, and incorporating wetting agents, and/or dispersing agents in such mixtures. The wettable powder then is diluted with water to form a liquid emulsion suitable for spraying.

Surfactants and other wetting agents, and dispersants, which may be included in the spray composition, provide complete contact with the fungus and/or adherance to the plants prior to fungus attack. Conventional nonionic surfactants which provide good wetting of the spray solution on the plant foliage or parts include alkyl polyoxyethylene ethers, polyoxyethylene (20) sorbitan monolaurate, polyoxyethylene (20) sorbitan monoleate, alkylarylpolyglycol ethers, alkyl phenol ethoxylates, trimethyl nonyl polyethylene glycol ethers, condensates of polyoxyethylenes, polyoxypropylenes, aliphatic polyethers, aliphatic polyesters, alkylaryl polyoxyethylene glycols, sulfonates, sulfates and the like.

Suitable dispersing agents include the calcium salt of a polymerized alkyl aryl sulfonic acid, sodium lignosulfonate, or sodium salt of condensed napthalene sulfonic acid. About 1% to 5%, by weight, of a surfactant, such as polyoxyethylated vegetable oil, alkyl phenoxy polyoxyethylene ethanol, sodium alkyl naphthalene sulfonate is often blended with the dispersant formulation.

A useful emulsifier blend of surfactant and dispersing agent is Atlox 3404F, made by ICI America, which is a blend of a calcium sulfonate dispersant and a nonionic surfactant; another comprises an aqueous 10% solution of acetone containing 50 to 300 ppm Triton surfactant based on an alkylaryl polyether alcohol, sulfonate, sulfate or phosphonate.

Alternatively, the compositions of the invention may be applied as a dust of particulate matter comprising the active ingredient in a solid powder, such as one or more of the above-mentioned extender diluents.

The fungicidal compositions of the invention generally are applied at a selected rate, preferably until the plants are drenched with the liquid spray, in an amount which will depend upon various circumstances, including the susceptibility of the plants to the fungus, the weather, the stage of growth and various other factors.

It is found that the present fungicides produce a controlled rate of activity over an extended period during the growing season and do not require repeated treatments at heavy dosage levels, as do the non-acylated analogs of the present compounds. Also, these fungicides are not harmful when in contact with plants, humans or animals.

The present fungicides and fungicidal compositions are useful for preharvest treatment of plants or postharvest treatment of crops and fruit since the present fungicides are substantially non-toxic or have very low levels of toxicity. Spraying the soil in which the plants or plant seeds are sown is also beneficial for contacting seedlings as they emerge from the soil with a light preventative fungicidal dosage; thereby rendering them more resistant to fungus attack.

Since the products of many plants are often marketed in a fresh condition, the time period between harvesting and consumption varies from one product to another but in most instances the period is at least several days in length. For certain products such as grapes and apples, the storage period may be several months in duration. The problem of keeping fresh fruit and vegetables in good condition for marketing is one of concern to plant pathologists. While proper handling to avoid wounding and the use of refrigeration, is beneficial it is often inadequate since many fungi, do not require a wound for entry or attack. On the other hand, refrigeration often succeeds only in slowing fungus activity but does not eliminate the problem. Accordingly, fungicides are employed in conjunction with refrigeration and careful handling. As stated hereinabove, the produce can be sprayed or dusted before or after harvest or, if the fruit is to be wrapped in individual papers, the wrappings can be impregnated with the fungicidal materials. This technique has been especially useful in preventing decay of peaches, pears and tomatoes. The present fungicides are also found to be useful for this type of wrapping impregnation.

Having generally described the invention, reference is now had to the accompanying examples which illustrate preferred embodiments but which are not to be construed as limiting to the scope of the invention as set forth above and as defined in the accompanying claims. All amounts and proportions recited in the following examples are by weight, unless otherwise indicated.

EXAMPLES 1-16

Representative alkyl aryl guanidines:

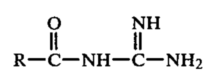

were selected for testing fungicidal properties against rust. Of the major leaf blights, rusts are the most pernicious fungi which attack above-ground parts of living plants. The ability of the present fungicides to protect non-infected foliage and eradicate infected tissue were evaluated along with internal systemic action.

Bean rust (*Uromyces phaseoli*) is representative of a large number of obligate parasites whose prolificacy in generating new parasitic strains has frequently frustrated efforts to control them by breeding for disease resistance. The present tests, results of which are reported in following Table I, were made on Pinto beans grown in 2.5 inch pots for 9 to 12 days by a combination of foliage spray and/or systemic protection from soil applications.

One and a half liter aqueous stock solutions of 10% acetone containing 1000 ppm surfactant (Triton X-155) and 520 ppm fungicidal agent were made up and diluted as required for the following experiments. Of these stock solutions, in Test A, 21 ml of the 520 ppm fungicide solution (equivalent to 25 lb/acre) was poured on the surface of the soil. At the same time the foliage was sprayed while rotating the plants on a turntable with 100 ml of the solution diluted to 250 ppm fungicide. After the spray deposit dried, the plants were atomized with a suspension of uredospores (summer spore stage) and placed in a moist chamber at 70° F. for 24 hours. After 7 days the severity of pustule formation was rated on a scale of 0 (no inhibition) to 10 (complete control) and compared to untreated controls. The same procedure was repeated for Test B except that the second series of plant were treated only with a foliar spray at various concentration levels.

The most active of the guanidine fungicides was then subjected to Tests A and B after the addition of equal amounts of a commercial herbicide (Lenacil) and one quarter amount of a commercial insecticide (Pyrolan) to the stock solutions at the above concentrations. The fungicide was substantially unimpared by the addition of these agricultural chemicals.

Finally, the results of the above tests were compared with those obtained from the leading commercial fungicides employed in the control of rusts, i.e. Plantvax and Vitavax. Results are reported in Table I below.

*imperfecti.* Tests were made on cucumber plants grown in 2.5 inch pots for 9-12 days by a combination of foliage spray and systemic protection with a soil drench. Employing stock solutions as prepared for the preceding examples, in Test A, 21 ml of a 520 ppm fungicide solution (equivalent to 25 lb/acre) were poured on the surface of the soil while the foliage was uniformly sprayed with 100 ml of solution diluted to 250 ppm fungicide by rotating the potted plant on a turntable. After the spray deposit dried, the treated plants were inoculated with a suspension of conidia in water and placed in a humidity chamber at 24° C. for 24 hours. Four days after inoculation, the number of lesions were counted, and results evaluated on a scale of 0 (no control) to 10 (100% control).

The same procedures used in the foregoing Tests A

TABLE I

| EXAMPLE | FUNGICIDE | TEST A. DEGREE OF CONTROL 260 PPM FOLIAR 25 lb/A. SOIL | RESIDUAL ACTIVITY AFTER 1 WEEK | TEST B. DEGREE OF CONTROL AT | | | | |
|---|---|---|---|---|---|---|---|---|
| | | | | 130 PPM | 65 PPM | 33 PPM | 16 PPM | 8 PPM |
| 1. | $C_7H_{15}-\overset{O}{\underset{\|\|}{C}}-NH-\overset{NH}{\underset{\|\|}{C}}-NH_2$ | 9.5 | V. Good | — | 8 | 7 | — | — |
| 2. | $C_8H_{17}-\overset{O}{\underset{\|\|}{C}}-NH-\overset{NH}{\underset{\|\|}{C}}-NH_2$ | 8.5 | Good | — | — | — | — | — |
| 3. | $C_9H_{19}-\overset{O}{\underset{\|\|}{C}}-NH-\overset{NH}{\underset{\|\|}{C}}-NH_2$ | 9.5 | V. Good | — | 8 | 7 | — | — |
| 4. | $C_{10}H_{21}-\overset{O}{\underset{\|\|}{C}}-NH-\overset{NH}{\underset{\|\|}{C}}-NH_2$ | 8 | Good | — | — | — | — | — |
| 5. | $C_{11}H_{23}-\overset{O}{\underset{\|\|}{C}}-NH-\overset{NH}{\underset{\|\|}{C}}-NH_2$ | 9.5 | Excellent | 10 | 10 | 10 | 10 | 10 |
| 6. | $C_{12}H_{25}-\overset{O}{\underset{\|\|}{C}}-NH-\overset{NH}{\underset{\|\|}{C}}-NH_2$ | 9 | Good | 9 | 7 | — | — | — |
| 7. | $C_{15}H_{31}-\overset{O}{\underset{\|\|}{C}}-NH-\overset{NH}{\underset{\|\|}{C}}-NH_2$ | 5.5 | Fair | — | — | — | — | — |
| 8. | $C_{17}H_{35}-\overset{O}{\underset{\|\|}{C}}-NH-\overset{NH}{\underset{\|\|}{C}}-NH_2$ | 6 | Fair | — | — | — | — | — |
| 9. | 50/50 mix. of compound 1 & 3 | 10 | Good | 7.5 | 6 | — | — | — |
| 10. | 50/50 mix. of compound 5 & 8 | 7.5 | Fair | — | — | — | — | — |
| 11. | No fungicide | 0 | — | — | — | — | — | — |
| 12. | Plantvax[a] supplied by Uniroyal, Inc. | 9 | — | — | — | — | — | — |
| 13. | Vitavax[b] supplied by Uniroyal, Inc. | — | | 10 | 10 | 8.5 | — | — |
| 14. | Daconil[e] supplied by Diamond Shamrock Co. | — | | 10 | 10 | 2 | 2 | — |
| 15. | 50/50 Mix. of Compound 5 and herbicide, Lenacil[c] of E. I. DuPont | 9 | — | — | — | 9 | 8 | — |
| 16. | 75/25 Mix. of Compound 5 and insecticide Pyrolan[d] | 9.5 | — | — | — | 9 | 8 | — |

[a] 5,6-dihydro-2-methyl-1,4-oxathiin-3-carboxanilide-4,4-dioxide
[b] 5,6-dihydro-2-methyl-1,4-oxathiin-3-carboxanilide
[c] 3-cyclohexyl-5,6-trimethyleneuracil
[d] 3-methyl-1-phenylpyrazol-5-yl dimethyl carbamate
[e] tetrachloroisophthalonitrile

EXAMPLES 17-27

Cucumber anthracnose (*Collectotrichum lagernarium*) is a representative of leaf blights caused by the *Fungi* and B were followed.

The results of these tests are reported in following Table II.

TABLE II

| EX-AMPLE | FUNGICIDE | TEST A. DEGREE OF CONTROL 260 PPM FOLIAR 25 lb/A. SOIL | TEST B. | | TEST C. DEGREE OF CONTROL AT | | |
|---|---|---|---|---|---|---|---|
| | | | 130 PPM | 65 PPM | 33 PPM | 16 PPM | 8 PPM |
| 17. | $C_7H_{15}\overset{O}{\underset{\|\|}{C}}-NH-\overset{NH}{\underset{\|\|}{C}}-NH_2$ | 8.5 | 8 | 8 | — | — | — |

TABLE II-continued

| EXAMPLE | FUNGICIDE | TEST A. DEGREE OF CONTROL 260 PPM FOLIAR 25 lb/A. SOIL | TEST B. 130 PPM | 65 PPM | TEST C. DEGREE OF CONTROL AT 33 PPM | 16 PPM | 8 PPM |
|---|---|---|---|---|---|---|---|
| 18. | $C_9H_{19}C(O)-NH-C(NH)-NH_2$ | 7 | — | — | — | — | — |
| 19. | $C_{10}H_{21}C(O)-NH-C(NH)-NH_2$ | 5.5 | — | — | — | — | — |
| 20. | $C_{11}H_{23}-C(O)-NH-C(NH)-NH_2$ | 10 | 10 | 10 | 9 | 6 | 5 |
| 21. | $C_{11}H_{23}-C(O)-NH-C(NH)-NH(CH_3)$ | 5.5 | — | — | — | — | — |
| 22. | $C_{15}H_{31}-C(O)-NH-C(NH)-NH_2$ | 5.5 | — | — | — | — | — |
| 23. | $C_8H_{17}CH=CHC_7H_{14}-C(O)-NH-C(NH)-NH_2$ | 3 | — | — | — | — | — |
| 24. | $C_8H_{17}C(O)-NH-C(NH)-NH(C_2H_5)$ | 7 | 6 | — | — | — | — |
| 25. | 50/50 Mix. of Compound 17 & 18 | 8 | 7 | 4 | 3 | — | — |
| 26. | Daconil | 9 | 10 | 10 | 10 | 2 | 2 |
| 27. | No Fungicide | 0 | — | — | — | — | — |

EXAMPLE 28

The procedure outlined for Examples 1-16 was repeated, except that 4.5 week old tomato seedlings were substituted for the bean plants and, after spraying the plants to drench with lauryl acyl guanidine, the tomatoes were infected with Alternaria Solani and Phytophthora infections, instead of rust, by atomizing the plants with a spore suspension. The plants were then incubated in a humidity cabinet at 70°-75° F. for 24 hours, after which they were held in the greenhouse until lesions appeared (3 days). The severity of the infection was rated on the scale of 0 to 10 and the results reported in following Table III.

Alternaria Solani and Pytophthora infestans are the most common members of the family of blights which attack tomatoes and potatoes.

TABLE III

| Fungicide: Concentration | $C_{11}H_{23}C(O)-NH-C(NH)-NH_2$ Early Blight | Late Blight |
|---|---|---|
| 260 ppm | — | 10 |
| 130 ppm | 9 | — |
| 65 ppm | 8 | 10 |
| 33 ppm | 4 | 10 |

EXAMPLE 29

Cucumber plants separately treated at the 2 leaf foliate stage with the compounds of Examples 4, 5 and 6 at a concentration of 130 ppm in aqueous solutions, then inoculated with the conidia of Erysiphe cichoracearum, placed in a humidity cabinet for 24 hours and then allowed to incubate for 10 days in a growth chamber at 70-75% humidity, simulating normal daylight and darkness conditions, show at least 75-80% control of infection over untreated plants, which indicates good systemic activity for a period of more than one week at low dosage levels. Residium on the plant and soil at this dosage level is negligible.

The results in the above tables demonstrate the effectiveness of the present process for the treatment of plants and plant parts with the fungicidal agents described herein. These agents, of low toxicity, are useful in the prevention of fungis attack or control of fungi infected plants or plant parts at extremely low concentrations at which they may display even higher efficacy than commercial fungicides currently employed.

While the invention has been described with reference to certain embodiments thereof, it will be understood that other fungicides heretofore recited and those falling within scope of the present claims can be substituted in any of the above experiments to provide good results. Similarly, other fungi, particularly the species of fungi classified as Deuteromycetes, Basidiomycetes and Pyrenonycetes can be substituted in the above and can be controlled by the fungicides of the present invention. It will be understood that many variations and modifications which are made obvious by the present description and disclosure can be made herein and are also included within the scope of this invention.

What we claim is:

1. A process for protecting plants and plant parts from attack by fungi which comprises contacting a plant or plant part with fungicidally effective amount of at least one fungicide having the formula:

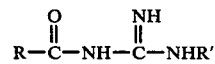

$$R-C(O)-NH-C(NH)-NHR'$$

wherein R is alkyl having from 4 to 22 carbon atoms and R' is hydrogen or alkyl of from 1 to 4 carbon atoms.

2. The process of claim 1 wherein said fungicide is employed in a composition containing an inert carrier.

3. The process of claim 2 wherein R' of said fungicide is hydrogen.

4. The process of claim 3 wherein said fungicide is:

$$C_{11}H_{23}-C(O)-NH-C(NH)-NH_2$$

5. A method according to claim 1 wherein said plant is contacted with a fungicide in the form of a solution, suspension, emulsion, wettable powder or dust.

6. A process according to claim 5 wherein said fungicide is applied as a liquid spray.

7. A process according to claim 5 wherein said fungicide is employed in a concentration of from about 3 ppm to about 3,000 ppm.

8. A process according to claim 7 wherein said fungicide is employed in a concentration of from about 5 ppm to about 800 ppm.

9. A process according to claim 1 wherein R of the fungicide is alkyl of from 6 to 16 carbon atoms.

10. A process according to claim 1 wherein said fungicide is sprayed onto living plants.

11. A process according to claim 4 wherein the fungicide is dodecylacyl guanidine.

12. A process according to claim 4 wherein the fungicide is nonylacyl guanidine.

13. A process according to claim 4 wherein the fungicide is heptylacyl guanidine alone or in admixture with nonylacyl guanidine.

14. A process according to claim 4 wherein the fungicide is undecylacyl guanidine.

15. A process according to claim 4 wherein the fungicide is octylacyl guanidine.

16. The process of claim 9 wherein a single fungicide compound is employed.

* * * * *